US009964558B2

(12) United States Patent
Yoshida

(10) Patent No.: US 9,964,558 B2
(45) Date of Patent: May 8, 2018

(54) AUTOMATIC ANALYZER

(71) Applicant: HITACHI HIGH-TECHNOLOGIES CORPORATION, Tokyo (JP)

(72) Inventor: Gorou Yoshida, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 27 days.

(21) Appl. No.: 15/109,824

(22) PCT Filed: Jan. 16, 2015

(86) PCT No.: PCT/JP2015/050999
§ 371 (c)(1),
(2) Date: Jul. 6, 2016

(87) PCT Pub. No.: WO2015/115200
PCT Pub. Date: Aug. 6, 2015

(65) Prior Publication Data
US 2016/0327586 A1    Nov. 10, 2016

(30) Foreign Application Priority Data

Jan. 30, 2014  (JP) .................................. 2014-015057

(51) Int. Cl.
*G01N 35/10*  (2006.01)
*G01N 35/00*  (2006.01)
(Continued)

(52) U.S. Cl.
CPC ... *G01N 35/1004* (2013.01); *G01N 35/00613* (2013.01); *G01N 35/00623* (2013.01);
(Continued)

(58) Field of Classification Search
None
See application file for complete search history.

(56) References Cited

U.S. PATENT DOCUMENTS 4,818,492 A * 4/1989 Shimizu ............... G01F 23/263
422/509
2002/0064481 A1  5/2002 Ishizawa et al.
(Continued)

FOREIGN PATENT DOCUMENTS

JP     05-256858 A    10/1993
JP     10-115623 A    5/1998
(Continued)

OTHER PUBLICATIONS

International Search Report of PCT/JP2015/050999 dated Apr. 21, 2015.
(Continued)

*Primary Examiner* — P. Kathryn Wright
(74) *Attorney, Agent, or Firm* — Mattingly & Malur, PC

(57) ABSTRACT

Dilution of a sample occurring in a sample dispensing operation is a problem in terms of analysis accuracy. Although the dilution amount is alleviated to some extent by a technique of sucking the sample excessively, the problem may emerge along with a requirement for reducing the sample dispensing amount, an increase of sucking and discharging speed in response to improvement of a processing capability, and an increase of the number of items to be analyzed simultaneously. Provided is an automatic analyzer including a mechanism monitoring conductivity of system water filled in a nozzle and an electro-physical amount such as voltage and capacitance of a probe to enable detection of mixture of the sample and a reagent into the system water and dilution of the sample and the reagent.

14 Claims, 3 Drawing Sheets

101. TRANSPORT LINE
102. ROTOR
103. REAGENT DISK
104. REACTION BATH
105. DISPENSATION MECHANISM
106. STIRRING MECHANISM
107. SPECTROSCOPE
108. REACTION CUVETTE CLEANING MECHANISM
109. NOZZLE CLEANING MECHANISM
110. SAMPLE CONTAINER
111. SAMPLE RACK
112. REACTION CUVETTE
113. REAGENT CONTAINER
115. CONTROL UNIT
116. NOZZLE
117. CAPACITANCE DETECTION MECHANISM

(51) Int. Cl.
*G01N 27/06* (2006.01)
*G01N 33/18* (2006.01)

(52) U.S. Cl.
CPC ..... *G01N 35/1002* (2013.01); *G01N 35/1009* (2013.01); *G01N 35/1016* (2013.01); *G01N 27/06* (2013.01); *G01N 33/18* (2013.01); *G01N 2035/00277* (2013.01); *G01N 2035/1025* (2013.01); *G01N 2035/1032* (2013.01)

(56) References Cited

U.S. PATENT DOCUMENTS

| | | |
|---|---|---|
| 2008/0286158 A1 | 11/2008 | Watanabe et al. |
| 2009/0000401 A1 | 1/2009 | Oonuma |
| 2010/0247383 A1* | 9/2010 | Okubo ................ G01N 27/06 422/82.02 |
| 2011/0184570 A1 | 7/2011 | Nakanishi et al. |

FOREIGN PATENT DOCUMENTS

| | | |
|---|---|---|
| JP | 2008-309777 A | 12/2008 |
| JP | 2010-190681 A | 9/2010 |

OTHER PUBLICATIONS

Extended European Search Report received in corresponding European Application No. 15743833.4 dated Oct. 9, 2017.

* cited by examiner

101. TRANSPORT LINE
102. ROTOR
103. REAGENT DISK
104. REACTION BATH
105. DISPENSATION MECHANISM
106. STIRRING MECHANISM
107. SPECTROSCOPE
108. REACTION CUVETTE CLEANING MECHANISM
109. NOZZLE CLEANING MECHANISM
110. SAMPLE CONTAINER
111. SAMPLE RACK
112. REACTION CUVETTE
113. REAGENT CONTAINER
115. CONTROL UNIT
116. NOZZLE
117. CAPACITANCE DETECTION MECHANISM

201. SPECIMEN
202. SYSTEM WATER
203. SEGMENTING AIR
204. NOZZLE
205. SAMPLE CONTAINER
206. MEASURED SPECIMEN
207. DUMMY SPECIMEN
208. HIGH-PRESSURE PUMP
209. STATE DURING INTERNAL CLEANING

AUTOMATIC ANALYZER

TECHNICAL FIELD

The present invention relates to dispensation control of an automatic analyzer.

BACKGROUND ART

An automatic analyzer for analyzing components in blood, urine, and the like is configured to dispense a liquid specimen and a reagent into a reaction cuvette to cause a chemical reaction, irradiate a reaction liquid with light by means of a halogen lamp or the like, and measure absorbance to analyze components in the liquid specimen.

A nozzle is used to dispense the sample and the reagent into the reaction cuvette. As water filling this nozzle, purified water supplied from a water purifying unit to a water feed tank of the analyzer is used and is called system water. A suction sequence is produced to prevent the sample and the reagent from contacting the system water in the nozzle and provide segmenting air therebetween.

When the sample and the system water move inside the nozzle during dispensation, movement between the sample and the system water may occur via an inner wall of the nozzle, and dilution of the sample may occur. To keep the dilution amount within an allowance, a dummy suction technique for sucking the sample excessively is disclosed (PTL 1).

Also, to prevent carry-over between samples, an internal cleaning operation for cleaning the inside of the nozzle is performed at the time of dispensing one sample and then another sample. The internal cleaning operation is performed with use of a high-pressure pump since the system water needs to be pushed out under high pressure for sufficient internal cleaning.

CITATION LIST

Patent Literature

PTL 1: JP 5-256858 A

SUMMARY OF INVENTION

Technical Problem

The dilution of the sample and the reagent may advance further than expected depending on the degree of dirtiness of the nozzle internal wall and the temperature of the system water and in a situation in which the segmenting air is not secured normally due to an abnormality inside the pipe.

Also, as for the internal cleaning performance, the high-pressure pump cannot generate enough pressure in case of a failure, deterioration, or a flow path abnormality, which causes a situation in which the internal cleaning is not performed sufficiently. When the internal cleaning is not performed sufficiently, contamination between samples will occur.

Either of the cases may have an effect on analysis accuracy.

Solution to Problem

Under an abnormal condition under which the segmenting air is not secured normally, it is estimated that the sample and the reagent diffuse into the system water side. In this situation, the system water in the piping tube connected to the nozzle acts as an electrode due to ions and the like in the sample and the reagent. The area of the system water acting as an electrode is added to the area of an electrode on the nozzle side, and a phenomenon in which the capacitance between the electrode on the nozzle side and a chassis increases is generated.

A representative invention is an automatic analyzer dispensing a sample and a reagent into a reaction cuvette and analyzing the sample with use of changes of absorbance of a reaction liquid reacted in the reaction cuvette, including: a dispensation nozzle dispensing either the sample or the reagent as a liquid into the reaction cuvette; a dispensation mechanism moving system water filled in the dispensation nozzle and causing the dispensation nozzle to suck and discharge the liquid via segmenting air; and a detection mechanism detecting conductivity of the system water.

Further, another representative invention is an automatic analyzer dispensing a sample and a reagent into a reaction cuvette and analyzing the sample with use of changes of absorbance of a reaction liquid reacted in the reaction cuvette, including: a dispensation nozzle dispensing either the sample or the reagent as a liquid into the reaction cuvette; a dispensation mechanism moving system water filled in the dispensation nozzle and causing the dispensation nozzle to suck and discharge the liquid via segmenting air; and a detection mechanism causing the dispensation nozzle to hold a charge and detecting an electro-physical amount that changes along with mixture of the liquid into the system water.

Advantageous Effects of Invention

According to the present invention, a decrease in analysis accuracy caused by the above problem can be restricted, and analysis accuracy can be improved.

BRIEF DESCRIPTION OF DRAWINGS

FIG. 3 illustrates an example of converting the changing amount of capacitance into a voltage value in a case in which dispensation is repetitively performed under a situation under which segmenting air is not secured normally or the like.

DESCRIPTION OF EMBODIMENTS

Hereinbelow, embodiments will be described with reference to the drawings.

Embodiment 1

Figure 1:
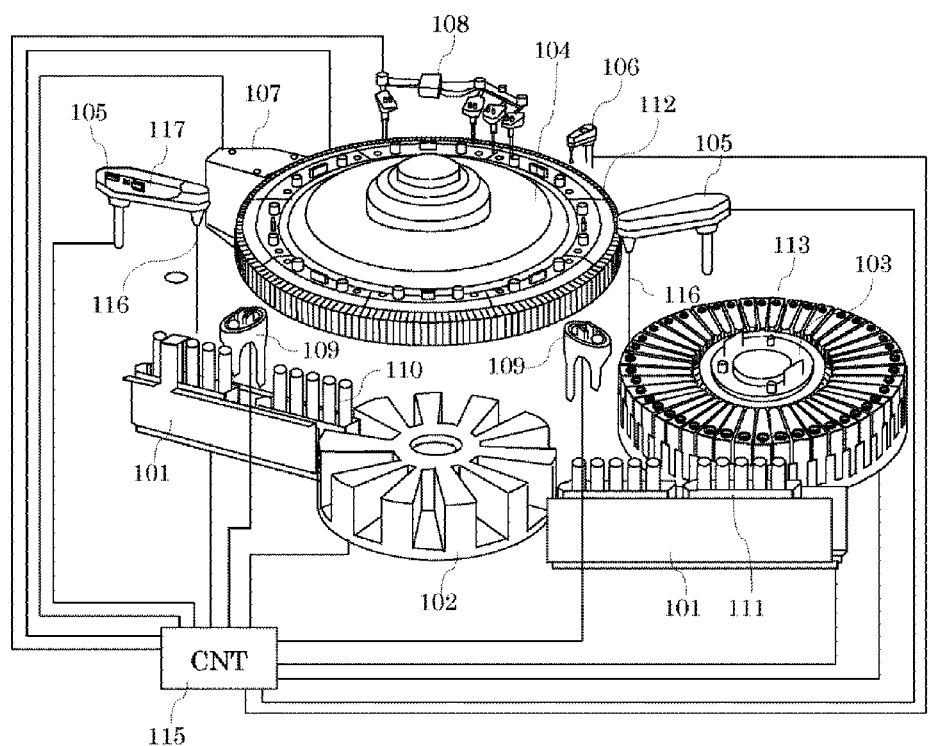
FIG. 1 illustrates a configuration example of an automatic analyzer.

FIG. 1 illustrates a configuration example of an automatic analyzer according to an embodiment of the present invention.

The automatic analyzer includes a transport line 101 and a rack rotor 102 transporting a sample container 110 containing a liquid specimen (for example, blood or urine as a sample), a reagent disk 103 setting a reagent container 113 in accordance with a measurement item, a reaction cuvette 112 causing the liquid specimen and a reagent to react and a reaction bath 104 serving as a holder of the reaction cuvette and configured to keep the reaction cuvette at constant temperature, a stirring mechanism 106 stirring a reaction to stabilize reaction of the liquid specimen dispensed into the reaction cuvette 112 and the added reagent, a spectroscope 107 measuring absorbance of the reaction liquid, a cleaning mechanism 108 sucking a waste liquid in the reaction cuvette and cleaning the reaction cuvette, a nozzle cleaning mechanism 109 cleaning an outer wall of a nozzle, a nozzle 116 partially collecting (dispensing) the liquid specimen or the reagent from the container, a capacitance detection mechanism 117 configured to detect a liquid level height of the specimen, and a control unit 115 controlling these mechanisms and calculating analysis results.

The sample container 110 is mounted in a sample rack 111 and is transported by the transport line 101. Meanwhile, although FIG. 1 is an example of an automatic analyzer in a transport-line type, the present invention can be applied to an automatic analyzer in a disk type.

The automatic analyzer also includes a dispensation mechanism 105 causing the nozzle 116 to suck and discharge a liquid. The dispensation mechanism 105 moves system water filled in the nozzle and causes the nozzle 116 to suck and discharge the liquid via segmenting air. The dispensation mechanism 105 includes a syringe configured to move the system water, and the movement is performed by actuation of this syringe. The dispensation mechanism 105 also includes a driving mechanism such as a motor driving the nozzle 116 into vertical and rotational movement.

An analysis method will be described. In the automatic analyzer, a sample as a liquid specimen and a reagent are dispensed into the reaction cuvette 112, and the sample is analyzed with use of changes of absorbance of a reaction liquid reacted in the reaction cuvette 112. First, a sample under analysis such as blood is held in the sample container 110 and is dispensed into the reaction cuvette 112 by the nozzle 116. On the other hand, a reagent is held in the reagent container 113 and is dispensed into the reaction cuvette 112 by a different nozzle 116 from the nozzle 116 for the sample. A reaction liquid is stirred and is irradiated with light from a light source, and the spectroscope 107 receives the light. Absorbance is calculated from the received light, and the control unit 115 calculates a concentration of a predetermined item contained in the sample from changes of the absorbance.

Figure 2:
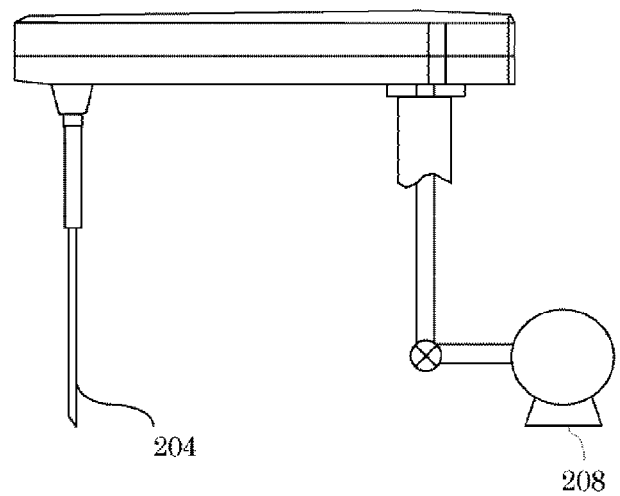
FIG. 2 illustrates an example of a dispensation mechanism and a state inside a nozzle during a dispensing operation.
Figure 2:
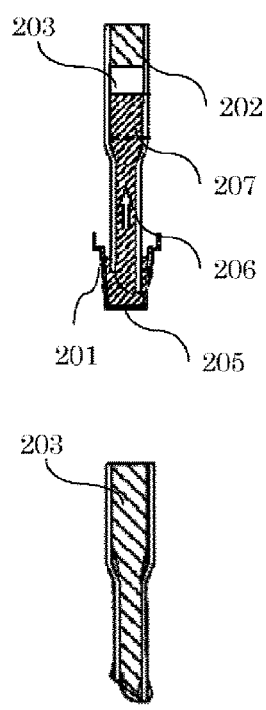

A liquid specimen dispensing method in the automatic analyzer configured as above will be described with reference to FIG. 2, which is an enlarged view of the sample dispensation mechanism. Meanwhile, although the sample dispensation mechanism will be described below, the present invention can be applied to the reagent dispensation mechanism. It is to be noted that a sample is also referred to as a specimen.

A high-pressure pump is connected to a flow path of a nozzle 204. First, to prevent contact between a specimen 201 and system water 202 in the nozzle and the flow path, segmenting air 203 is sucked. Subsequently, the nozzle 204 is rotated and lowered over a specimen container 205 (sample container 110) and detects a liquid level. At this time, the nozzle 204 sucks not only a measured specimen 206 but also a dummy specimen 207 for eliminating a dilution effect of the specimen. Thereafter, the specimen probe is raised, rotated, moved to a place over the reaction cuvette, and lowered to a bottom of the reaction cuvette, and discharges the specimen. At this time, as for the discharge of the specimen, the probe discharges only the measured specimen into the reaction cuvette without discharging the dummy specimen 207. Lastly, the probe moves to a cleaning bath. The external wall of the probe is cleaned by means of an external cleaning operation, in which the external wall of the prove is sprayed with cleaning water while the internal part of the probe is cleaned by means of an internal cleaning operation, in which the system water supplied from a water feed tank and pressurized by a high-pressure pump 208 is pushed out. During the internal cleaning, the system water is pushed out by the high-pressure pump as illustrated by reference sign 209. However, the internal cleaning operation is not performed when the same sample is repetitively dispensed but is performed when a subsequent sample is to be dispensed.

Next, a method for detecting an electro-physical amount that changes along with mixture of the sample into the system water will be described. The electro-physical amount used here means a voltage value, a capacitance value, or the like.

Figure 3:
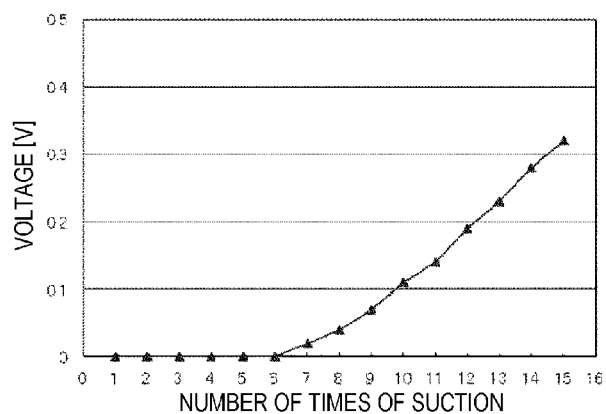

FIG. 3 illustrates an example of voltage changes generated as the system water acts as an electrode in a case in which dispensing operations are repetitively performed without doing the internal cleaning operation under a situation under which the segmenting air is not secured normally or under an abnormal condition under which the amount of the segmenting air is decreased to easily cause contamination. Hereinbelow, an example using a capacitance value will be described. Meanwhile, FIG. 3 illustrates data in which the changing amount of the capacitance has been converted into a voltage value. Also, the changing amount of the capacitance is measured at an uppermost position to which the probe can move after the nozzle has sucked the liquid and before dispensation. Also, this capacitance is a value between the nozzle and a GND level, and the converted voltage value is a value between the nozzle and the GND level as well.

As an output value of the capacitance detection mechanism 117, a capacitance value C1 at a position at which the nozzle 116 (204) does not contact the specimen, such as an uppermost position, is used. The nozzle 116 (204) is made of a conductive material. In a case in which movement of the system water is repeated during dispensation under an abnormal condition under which the segmenting air is not secured normally, mutual contamination occurs between the sample and the system water. As a result, since the sample contains ions such as electrolytes, the system water, which has low conductivity because the system water is purified water, becomes conductive. Accordingly, by providing a detection mechanism detecting conductivity of the system water, mixture of the sample into the system water can be detected.

On the other hand, from a viewpoint of the nozzle 116 (204), the capacitance value measured in the capacitance detection mechanism 117 changes from one in a state in which no contamination occurs because the system water becomes conductive.

When the system water becomes conductive and electrically contacts an electrode on the nozzle side, it is estimated that a deemed area of the electrode on the nozzle side will increase. Since a circuit in which the voltage increases as the capacitance on the nozzle side increases is incorporated, the capacitance increases when the deemed area of the electrode increases because the system water becomes conductive, and the voltage gradually increases as in FIG. 3. Also, since the capacitance increases when the conductivity of the system water increases, the voltage value gradually increases as in FIG. 3. Accordingly, by providing a detection mechanism detecting the voltage value or the capacitance value as the electro-physical amount in the nozzle 116 (204), mixture of the sample into the system water can be detected. Conversely, in a case in which a circuit in which the voltage decreases as the capacitance on the nozzle side increases is incorporated, the voltage value changes to a negative side.

Also, in a case in which, in the future, the dispensation speed is desired to be raised while the dispensation accuracy is maintained, the case will bring about a situation in which it is preferable to decrease the amount of the segmenting air as much as possible for the purpose of restricting an effect of responsiveness of the segmenting air. In this case, it is estimated that dilution of the sample due to the system water will occur easily. When the sample side is diluted, it is estimated that the sample is partially mixed into the system water side. Thus, by clarifying the dilution amount and the changing amount of the capacitance in advance, the vertical axis in FIG. 3 can be converted into the dilution amount, and it is possible to determine whether the dilution amount is within an allowable range. That is, based on relationship between the dilution amount of the liquid due to the system water and the changing amount of the electro-physical amount stored in advance in a storage unit having stored therein the relationship and the allowable range of the dilution amount, the changing amount of the electro-physical amount detected by the detection mechanism can be converted into the dilution amount of the liquid. This conversion can be performed by the control unit 115, and the control unit 115 can also determine whether the converted dilution amount is within the stored allowable range. Also, this determination can be applied to the conductivity of the system water and the electro-physical amount.

Accordingly, by performing such determination with use of this detection mechanism, in a case in which the conductivity of the system water, the electro-physical amount, or the dilution amount exceeds the allowable value, a decrease in analysis accuracy due to dilution can be prevented by combination of processing of interrupting dispensation, continuation of the analysis by internal cleaning and a re-dispensing operation, and processing of setting a data flag. That is, in a case in which the above allowable value is exceeded before the nozzle dispenses the liquid into the reaction cuvette, the control unit 115 desirably performs any one of (1) interrupting dispensation of the liquid, (2) performing internal cleaning of the dispensation nozzle, making new system water held in the dispensation nozzle, and performing dispensation of the same liquid again, and (3) continuing dispensation of the liquid and setting a data flag to an analysis result obtained when the liquid continuously dispensed is used. Meanwhile, setting a data flag means putting a mark on a measurement result to distinguish between a measurement result measured within the allowable range and a measurement result measured out of the allowable range. Meanwhile, another threshold value may be set in the range of the allowable values, and the control unit may perform any one of the above processing after the value exceeds this threshold value and before the value exceeds the allowable value. In this case, this threshold value can be regarded as an allowable value.

Meanwhile, as illustrated in FIG. 3, there is a tendency to easily exceed the allowable value when the dispensing operations are repeated, but in a case in which the severity of the situation in which the segmenting air is not secured normally is significant, any one of the above methods (1) to (3) can be employed even when repetitive dispensation of the same liquid is not to be performed. On the other hand, when the repetitive dispensation of the same liquid is to be performed, and when the above method (3) is to be performed, it is desirable not to set a data flag to an analysis result obtained when the liquid dispensed into the reaction cuvette before the allowable value is exceeded is used and to set a data flag to an analysis result obtained when the liquid dispensed into the reaction cuvette after the allowable value is exceeded even in dispensation of the same liquid is used. In this case, it is desirable to perform dispensation as many times of dispensation as planned.

Figure 4:
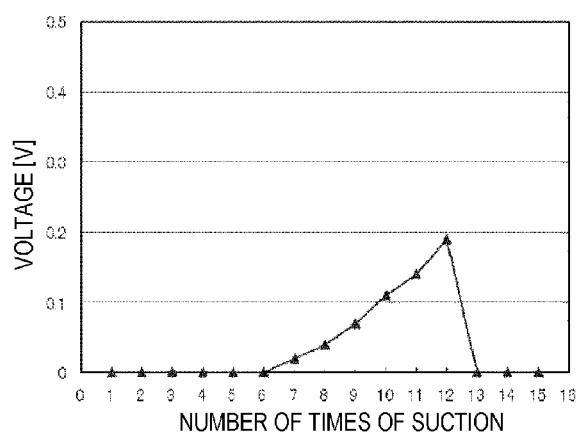
FIG. 4 illustrates an example of voltage changes in a case in which internal cleaning is performed in the middle of dispensation.

FIG. 4 illustrates an example of voltage changes in a case in which the same liquid is repetitively dispensed while the system water is held, and in which internal cleaning is performed in the middle of the dispensation. This example is an example in which dilution is solved by the internal cleaning and the re-dispensing operation. In a case in which dilution equivalent to 0.2 V of voltage is an allowable limit, it can be predicted that the allowable value will be exceeded at the 13th dispensation as illustrated in FIG. 4. Thus, by performing the internal cleaning operation after the 12th dispensation, dilution is solved, and the analysis can be continued within the allowable range. Meanwhile, the same can be applied to the conductivity of the system water and the electro-physical amount.

In the above description, an example in which the capacitance value as an electro-physical amount is detected at the uppermost position of vertical driving of the nozzle is illustrated. However, the conductivity of the system water and the electro-physical amount have only to be detected at a time when the nozzle is at the same height each time of dispensation, and the present invention is not limited to detection at the uppermost position. In other words, timing does not manner as long as detection can be done under the same height condition. In a case of detecting different samples, detection timing may differ per sample. However, in a case of repetitively dispensing the same liquid while the dispensation nozzle is holding the system water, detection is performed at a time when the dispensation nozzle is at the same height in order to do so under the same height condition. However, since the uppermost position of the vertical driving of the nozzle is a position farthest away from the analyzer and farthest away from the sample container, which may cause changes of the capacitance and the like, the uppermost position is relatively electrically stable, and detection at this position is most preferable.

Also, in the above description, an example in which the capacitance detection mechanism detects the electro-physical amount is illustrated. However, this capacitance detection mechanism can also detect the conductivity of the system water by calculating the conductivity from the electro-physical amount. The reason for this is that the degree of conductivity of the system water changes in accordance with the degree of change of the capacitance. Meanwhile, as another detection mechanism, a pair of electrodes may be provided in the pipe filled with the system water, and the conductivity of the system water may be detected from a voltage value and a resistance value between the electrodes. However, there is a nozzle provided with a capacitance detection mechanism detecting the liquid level height of the sample by detecting the changing amount of the capacitance. In this case, this capacitance detection mechanism and the above detection mechanism may be integrated to incorporate the capacitance detection mechanism into the detection mechanism. That is, a single detection mechanism may perform detection of the liquid level height and detection of the conductivity and the electro-physical amount according to the present invention. In this case, since a circuit can be shared, the sharing leads to merits such as reduction in the number of parts and size reduction.

Embodiment 2

In the present embodiment, an example of an analyzer determining whether cleaning by the internal cleaning operation is sufficient will be described. In Embodiment 1 is described detection of mixture of the sample into the system water in the case of repetitively dispensing the same sample. With a similar configuration, the degree of cleaning by the internal cleaning, a failure or deterioration of the pump supplying the nozzle with the system water to be used in the internal cleaning, and an abnormality of the flow path or the like of the system water can be detected.

To prevent carry-over between samples, the internal cleaning operation for cleaning the inside of the nozzle is performed at the time of dispensing one sample and then another sample. The internal cleaning operation is performed with use of the high-pressure pump 208 since the system water needs to be pushed out under high pressure for sufficient internal cleaning. At this time, the high-pressure pump cannot generate enough pressure in case of the failure, the deterioration, or the flow path abnormality, and the internal cleaning is not performed sufficiently. At this time, in a case in which contamination of the system water with the sample during sample dispensation is not solved sufficiently, the capacitance value as the electro-physical amount at the uppermost position changes from one in a state in which no contamination occurs. The degree of cleaning can be determined from this changing amount. That is, the control unit 115 can compare an electro-physical amount, detected by the detection mechanism in a state in which the nozzle is filled with the system water after the internal cleaning of the nozzle is performed, with a reference value, and can determine the degree of cleaning by the internal cleaning based on the comparison result. The reason for this is that, in a case in which contamination is not solved sufficiently, the sample is mixed into the system water, the conductivity of the system water becomes higher than the conductivity of purified water, and a similar phenomenon to that in Embodiment 1 occurs.

By determining the above degree of cleaning, any of the failure of the pump supplying the dispensation nozzle with the system water to be used in the internal cleaning, the deterioration thereof, and the abnormality of the flow path of the system water can be detected.

On the other hand, a situation in which the changing amount is extremely small, such as a case in which the dispensation amount is small and a case in which the number of analysis items is low, is assumed. In this case, a difference of characteristics due to a difference of conductivity illustrated in FIG. 5 can be used.

Figure 5:
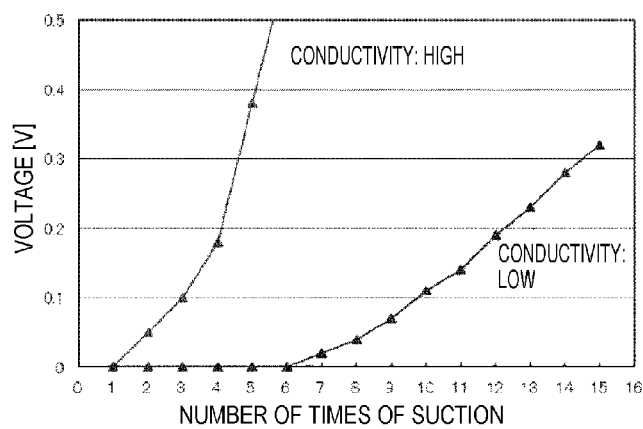
FIG. 5 illustrates an example of a difference of voltage changes due to a difference of conductivity of sucked liquids.

FIG. 5 illustrates a difference of voltage changes due to a difference of conductivity of sucked liquids and illustrates relationship between the number of times of suction and voltage changes due to the difference of conductivity. In general, blood as a sample has low conductivity, and detergent has higher conductivity than the sample. For this reason, by dispensing the detergent before the internal cleaning, the system water becomes conductive more easily when a comparison is made with the same number of times of dispensation.

Thus, by detecting the electro-physical amount at a time after a highly-conductive liquid such as detergent is dispensed, such as a time of cleaning the nozzle and a time of adding Hitergent to the reaction bath, the above abnormalities can be detected more accurately even in a case in which the number of times of suction is low, such as a case in which the dispensation amount is small and a case in which the number of analysis items is low. Accordingly, it is an effective method to perform the internal cleaning after the nozzle has dispensed the detergent and detect the electro-physical amount in a state in which the nozzle is filled with the system water before dispensing another sample to determine the degree of cleaning. Meanwhile, in a case in which the conductivity of the detergent is extremely high, the above abnormalities can be detected even in a case of single sample suction, as well as in a case of plural times of suction.

Also, as processing to be performed when it is determined that cleaning is not sufficient, backup processing, such as performing cleaning again while monitoring the electro-physical amount, interrupting the analysis operation, and continuing the analysis and setting a data flag, is effective. That is, any of the above methods (1) to (3) in Embodiment 1 can be employed.

Meanwhile, in Embodiment 2 as well, the present invention can be applied not only to the sample dispensation mechanism but also to the reagent dispensation mechanism. Since other matters are similar to those in Embodiment 1, description thereof is omitted.

REFERENCE SIGNS LIST 101 transport line
102 rotor
103 reagent disk
104 reaction bath
105 dispensation mechanism
106 stirring mechanism
107 spectroscope
108 reaction cuvette cleaning mechanism
109 nozzle cleaning mechanism
110 sample container
111 sample rack
112 reaction cuvette
113 reagent container
115 control unit
116 nozzle
117 capacitance detection mechanism
201 specimen
202 system water
203 segmenting air
204 nozzle
205 sample container
206 measured specimen
207 dummy specimen
208 high-pressure pump
209 state during internal cleaning

The invention claimed is:
1. An automatic analyzer to analyze a sample and a reagent which react into a reaction liquid in a reaction cuvette using absorbance of the reaction liquid, the automatic analyzer comprising:
a dispensation nozzle configured to contain system water and segmenting air;

a dispensation mechanism configured to move the system water in the dispensation nozzle;

a detection mechanism configured to detect a conductivity of the system water in the dispensation nozzle;

a spectroscope configured to measure absorbance of the reaction liquid;

a storage unit having stored therein in advance a relationship between a dilution amount of the liquid due to the system water and a changing amount of the detected conductivity and an allowable range of the dilution amount; and a control unit to control operations of the dispensation nozzle, the dispensation mechanism, the detection mechanism, and the spectroscope, wherein the control unit is programmed to:

control the dispensation mechanism to move the system water in the dispensation nozzle and cause the dispensation nozzle to suck either the sample or the reagent as a liquid, the liquid being separated from the system water in the dispensation nozzle by the segmenting air, and discharge the liquid into the reaction cuvette, convert an amount of change in the detected conductivity into a dilution amount of the liquid based on the relationship between dilution of the liquid due to mixing with the system water and conductivity of the system water stored in the storage unit, and control the dispensation mechanism based on whether the dilution amount of the liquid is within a predetermined allowable range.

2. The automatic analyzer according to claim 1, wherein, when the detected conductivity of the system water in the dispensation nozzle exceeds the predetermined allowable range before the dispensation nozzle dispenses the liquid into the reaction cuvette, the control unit is further programmed to perform one of:

interrupting the dispensation of the liquid, performing internal cleaning of the dispensation nozzle, providing new system water in the dispensation nozzle, and performing dispensation of the same liquid again, and continuing dispensation of the liquid and storing a data flag for the measured absorbance of the reaction liquid.

3. The automatic analyzer according to claim 2, wherein the detection mechanism includes a capacitance detector configured to detect a liquid level height of the liquid.

4. An automatic analyzer to analyze a sample and a reagent which react into a reaction liquid in a reaction cuvette using absorbance of the reaction liquid, the automatic analyzer comprising:

a dispensation nozzle configured to contain system water and segmenting air:

a dispensation mechanism configured to move the system water in the dispensation nozzle;

a detection mechanism configured to detect an electro-physical amount of the system water in the dispensation nozzle;

a spectroscope configured to measure absorbance of the reaction liquid;

a storage unit having stored therein in advance a relationship between a dilution amount of the liquid due to the system water and a changing amount of the detected electro-physical amount and an allowable range of the dilution amount; and a control unit to control operations of the dispensation nozzle, the dispensation mechanism, the detection mechanism, and the spectroscope, wherein the control unit is programmed to:

control the dispensation mechanism to move the system water in the dispensation nozzle and cause the dispensation nozzle to suck either the sample or the reagent as a liquid, the liquid being separated from the system water in the dispensation nozzle by the segmenting air, and discharge the liquid into the reaction cuvette, convert an amount of change in the detected electro-physical amount into a dilution amount of the liquid based on the relationship between dilution of the liquid due to mixing with the system water and values of the electro-physical amount stored in the storage unit, and control the dispensation mechanism based on whether the dilution amount of the liquid is within a predetermined allowable range.

5. The automatic analyzer according to claim 4, wherein, when the detected electro-physical amount of the system water in the dispensation nozzle exceeds the predetermined allowable range before the dispensation nozzle dispenses the liquid into the reaction cuvette, the control unit is further programmed to perform one of:

interrupting the dispensation of the liquid, performing internal cleaning of the dispensation nozzle, providing new system water in the dispensation nozzle, and performing dispensation of the same liquid again, and continuing dispensation of the liquid and storing a data flag for the measured absorbance of the reaction liquid.

6. The automatic analyzer according to claim 5, wherein the control unit is further programmed to:

control dispensation mechanism to repetitively dispense the same liquid from the dispensation nozzle while the system water is held therein, the dispensation mechanism repeating vertical driving and rotational driving of the dispensation nozzle when repetitively dispensing the same liquid, and wherein the detection mechanism detects the electro-physical amount at a time when the dispensation nozzle is at a same height for each time of dispensation to detect the mixture of the liquid into the system water.

7. The automatic analyzer according to claim 6, wherein the same height is an uppermost position of the vertical driving of the dispensation nozzle.

8. The automatic analyzer according to claim 4, wherein the control unit is further programmed to:

perform internal cleaning of the dispensation nozzle, compare the detected electro-physical amount, detected by the detection mechanism when the dispensation nozzle is filled with the system water after the internal cleaning of the dispensation nozzle is performed, with a predetermined reference value, and determine a degree of cleaning by the internal cleaning based on the comparison.

9. The automatic analyzer according to claim 8, wherein the control unit is further programmed to detect any of a failure of a pump supplying the dispensation nozzle with the system water to be used in the internal cleaning, deterioration thereof, and an abnormality of a flow path of the system water based on the determined degree of cleaning.

10. The automatic analyzer according to claim 9, wherein the internal cleaning is internal cleaning after the dispensation nozzle has dispensed a detergent and before the dispensation nozzle dispenses another liquid.

11. The automatic analyzer according to claim 4, wherein the detection mechanism detects a liquid level height of the sucked liquid by detecting the changing amount of capacitance as the electro-physical amount.

12. The automatic analyzer according to claim 11, wherein the electro-physical amount is a voltage value or a capacitance value of the dispensation probe.

13. The automatic analyzer according to claim 8, wherein the detection mechanism detects a liquid level height of the sucked liquid by detecting the changing amount of capacitance as the electro-physical amount.

14. The automatic analyzer according to claim 8, wherein the electro-physical amount is a voltage value or a capacitance value measured at the dispensation nozzle.

* * * * *